(12) United States Patent
McEwen et al.

(10) Patent No.: US 9,931,126 B2
(45) Date of Patent: *Apr. 3, 2018

(54) PERSONALIZED TOURNIQUET METHODS AND APPARATUS

(71) Applicant: Western Clinical Engineering Ltd., Vancouver (CA)

(72) Inventors: James A. McEwen, Vancouver (CA); Michael Jameson, North Vancouver (CA); Jeswin Jeyasurya, Vancouver (CA); Kenneth L. Glinz, Richmond (CA)

(73) Assignee: Western Clinical Engineering Ltd., Vancouver (CA)

( * ) Notice: Subject to any disclaimer, the term of this patent is extended or adjusted under 35 U.S.C. 154(b) by 328 days.

This patent is subject to a terminal disclaimer.

(21) Appl. No.: 14/837,999

(22) Filed: Aug. 27, 2015

(65) Prior Publication Data
US 2016/0008006 A1    Jan. 14, 2016

Related U.S. Application Data

(63) Continuation-in-part of application No. 14/696,401, filed on Apr. 25, 2015, which is a continuation of
(Continued)

(51) Int. Cl.
*A61B 17/00* (2006.01)
*A61B 17/135* (2006.01)
(Continued)

(52) U.S. Cl.
CPC ...... *A61B 17/1355* (2013.01); *A61B 5/02233* (2013.01); *A61B 5/022* (2013.01);
(Continued)

(58) Field of Classification Search
CPC . A61B 17/132; A61B 17/1322; A61B 17/135; A61B 17/1355; A61B 5/022; A61B 5/02233
See application file for complete search history.

(56) References Cited

U.S. PATENT DOCUMENTS 4,210,147 A * 7/1980 Nestor ................ A61B 17/132
606/202
4,349,034 A    9/1982 Ramsey, III
(Continued)

FOREIGN PATENT DOCUMENTS

JP    63-317131    12/1988
WO   WO198300995   3/1983
WO   WO2007016772  2/2007

OTHER PUBLICATIONS

McEwen, J. et al., An Adaptive Tourniquet for Improved Safety in Surgery, IEEE Transactions on Biomedical Engineering, Feb. 1982, 7 pages, vol. BME-29, No. 2.
(Continued)

*Primary Examiner* — Robert Lynch
(74) *Attorney, Agent, or Firm* — Klarquist Sparkman, LLP

(57) ABSTRACT

Disclosed are methods and apparatus for regulating tourniquet cuff pressure based on a personalized tourniquet pressure (PTP) to facilitate safe performance of surgical and medical procedures. The apparatus includes a dual-purpose tourniquet cuff adapted to encircle a region of a patient to provide both a sensor during a first time period and an effector during a second time period. An effector module communicates pneumatically with an inflatable bladder of the cuff for maintaining pressure in the bladder near a PTP during the second time period to safely stop penetration of arterial blood past the cuff. A pulsation sensor that communicates pneumatically with the inflatable bladder during the
(Continued)

first time period senses and characterizes pressure pulsations that are indicative of penetration of arterial blood into the region of a patient encircled by the cuff. A PTP estimator is responsive to the pulsation sensor for producing an estimate of the PTP, such that the estimate of the PTP is a function of the sensed pulsations.

35 Claims, 11 Drawing Sheets

Related U.S. Application Data application No. 14/328,607, filed on Jul. 10, 2014, now Pat. No. 9,039,730.

(51) Int. Cl.
| | | |
|---|---|---|
| A61B 5/022 | (2006.01) | |
| A61B 17/132 | (2006.01) | |
| A61B 90/92 | (2016.01) | |
| A61B 90/98 | (2016.01) | |
| A61B 90/00 | (2016.01) | |

(52) U.S. Cl.
CPC ............ *A61B 17/132* (2013.01); *A61B 17/135* (2013.01); *A61B 17/1322* (2013.01); *A61B 90/92* (2016.02); *A61B 90/98* (2016.02); *A61B 2017/00022* (2013.01); *A61B 2017/00119* (2013.01); *A61B 2017/00199* (2013.01); *A61B 2090/0807* (2016.02); *A61B 2505/05* (2013.01); *A61B 2562/08* (2013.01)

(56) References Cited

U.S. PATENT DOCUMENTS

| | | | |
|---|---|---|---|
| 4,469,099 A | 9/1984 | McEwen |
| 4,479,494 A | 10/1984 | McEwen |
| 5,254,087 A | 10/1993 | McEwen |
| 5,439,477 A | 8/1995 | McEwen |
| 5,503,156 A | 4/1996 | Millar |
| 5,556,415 A | 9/1996 | McEwen |
| 5,584,853 A | 12/1996 | McEwen |
| 5,855,589 A | 1/1999 | McEwen |
| 5,911,735 A | 6/1999 | McEwen |
| 6,050,951 A | 4/2000 | Friedman |
| 6,319,205 B1 | 11/2001 | Goor |
| 6,322,515 B1 | 11/2001 | Goor |
| 6,605,103 B2 | 8/2003 | Hovanes et al. |
| 6,939,304 B2 | 9/2005 | Schnall |
| 7,479,154 B2 | 1/2009 | McEwen |
| 7,485,131 B2 | 2/2009 | Hovanes et al. |
| 7,771,453 B2 | 8/2010 | McEwen |
| 8,083,763 B2 | 12/2011 | McEwen |
| 8,366,740 B2 | 2/2013 | McEwen et al. |
| 8,425,426 B2 | 4/2013 | McEwen et al. |
| 2004/0147956 A1 | 7/2004 | Hovanes |
| 2006/0253150 A1 | 11/2006 | McEwen |
| 2007/0167844 A1 | 7/2007 | Asada |
| 2009/0112104 A1 | 4/2009 | Usuda et al. |
| 2009/0124912 A1 | 5/2009 | McEwen et al. |
| 2010/0324429 A1 | 12/2010 | Leschinsky |
| 2013/0144330 A1 | 6/2013 | McEwen |
| 2013/0190806 A1 | 7/2013 | McEwen et al. |
| 2013/0211445 A1 | 8/2013 | McEwen |
| 2013/0226013 A1 | 8/2013 | McEwen et al. |

OTHER PUBLICATIONS

Miller, M. et al., A Near-Optimum Filter for Suppressing Motion Artifact in Oscillometric Signals, IEEE Engineering in Medicine & Biology Soc. 11th Annual Int'l Conf., Jun. 1989, 2 pages.

Miller, M., Estimation of Limb Occlusion Pressure by Adaptation of Oscillometry for Surgical Tourniquet Systems, Thesis, University of British Columbia, Dec. 1989, 136 pages.

Bussani, C. et al., Improved Tracking of Limb Occlusion Pressure for Surgical Tourniquets, IEEE Transactions on Biomedical Engineering, Apr. 1988, 9 pages, vol. BME-35, No. 4.

Bussani, C., Improved Noninvasive Determination of Blood Pressure by Oscillometry in the Presence of Motion Artifacts, Thesis, University of British Columbia, Jun. 1986, 142 pages.

International Search Report and Written Opinion for PCT/CA2015/050385 (dated Jul. 14, 2015).

* cited by examiner

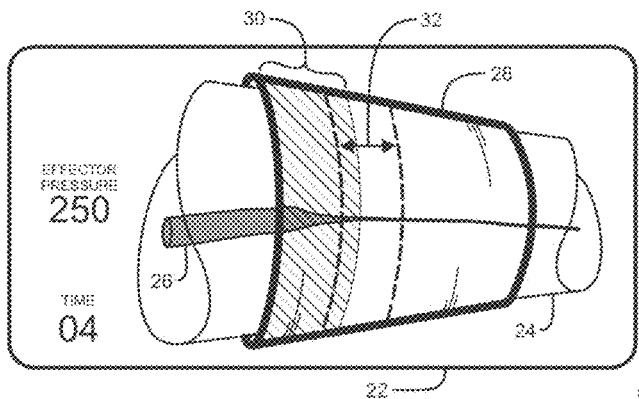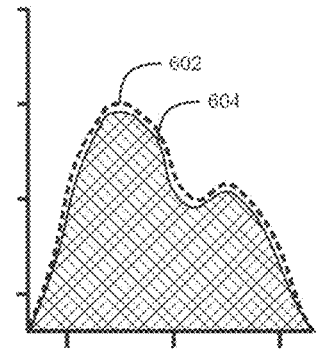
FIG. 6a
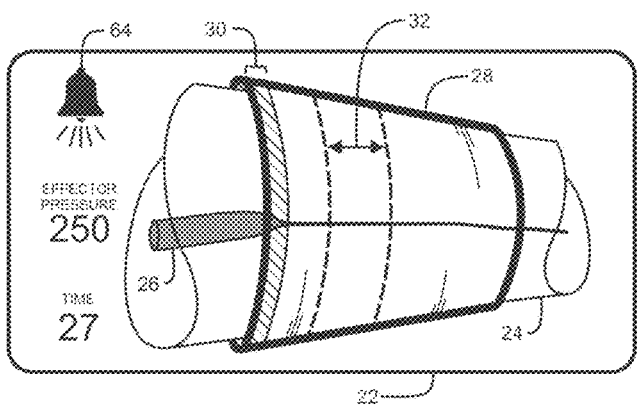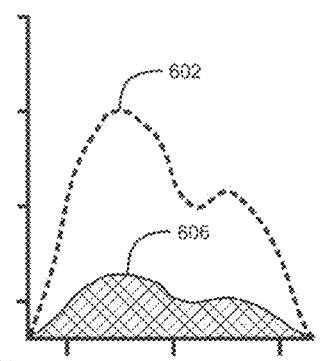
FIG. 6b
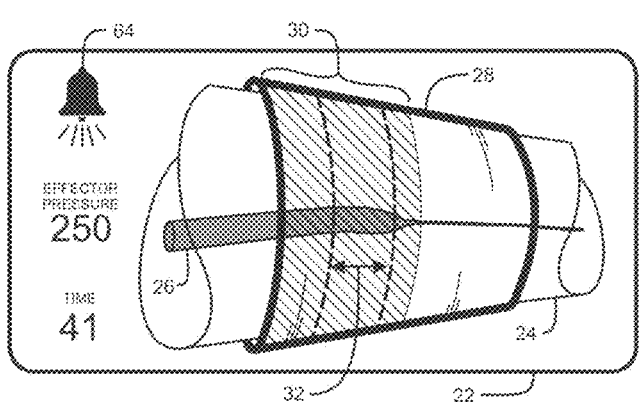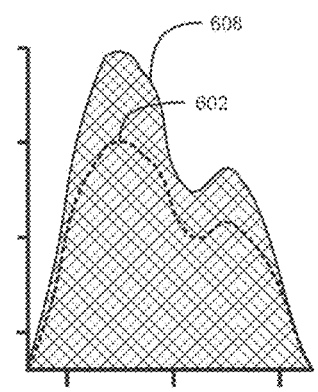
FIG. 6c

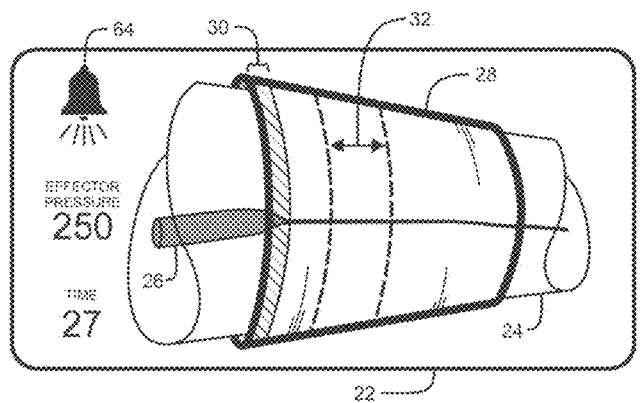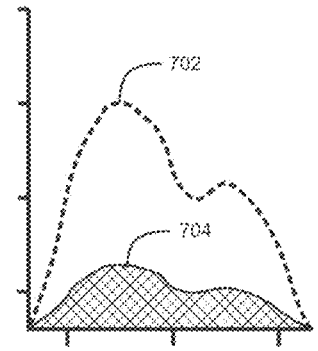
FIG. 7a
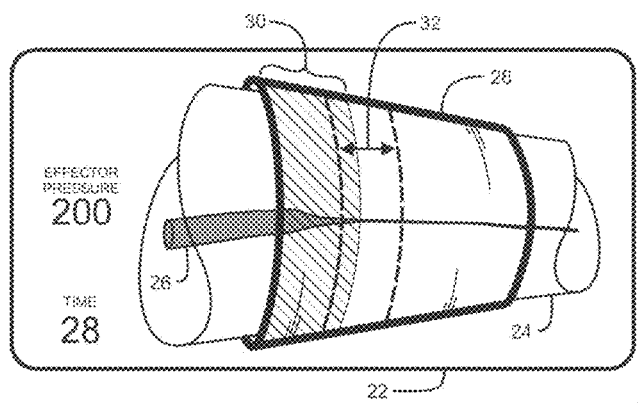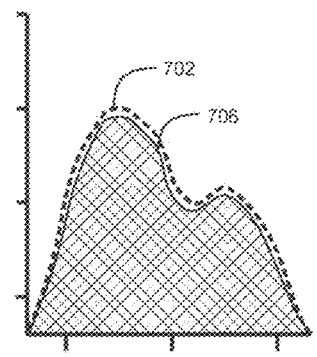
FIG. 7b

PERSONALIZED TOURNIQUET METHODS AND APPARATUS

CROSS REFERENCE TO RELATED APPLICATION

This application is a continuation-in-part of U.S. patent application Ser. No. 14/696,401, filed Apr. 25, 2015, which is a continuation of U.S. patent application Ser. No. 14/328,607, filed Jul. 10, 2014, now U.S. Pat. No. 9,039,730, both of which are incorporated herein by reference.

FIELD

This invention pertains to pneumatic tourniquet systems commonly used for stopping the penetration of arterial blood into a region of a patient to facilitate the performance of a surgical or medical procedure. In particular, this invention pertains to a pneumatic tourniquet methods and apparatus for establishing and maintaining a personalized tourniquet pressure for a period of time.

BACKGROUND

Surgical tourniquet systems are commonly used to stop the penetration of arterial blood into a portion or region of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible tubing connecting the cuff to the instrument. In some surgical tourniquet systems of the prior art, the tourniquet cuff includes an inflatable bladder that is connected pneumatically to a tourniquet instrument via flexible tubing attached to one or two cuff ports. The tourniquet instrument includes a pressure regulator to maintain the pressure in the inflatable bladder of the cuff near a reference pressure that is above a minimum pressure required to stop arterial blood penetration past the cuff, when applied to a patient's limb at a desired location during a time period suitably long for the performance of a surgical procedure. Many types of such pneumatic surgical tourniquet systems have been described in the prior art, such as those described by McEwen in U.S. Pat. No. 4,469,099, U.S. Pat. No. 4,479,494, U.S. Pat. No. 5,439,477 and by McEwen and Jameson in U.S. Pat. No. 5,556,415 and U.S. Pat. No. 5,855,589.

Tourniquet cuffs of the prior art are designed to serve as effectors which apply high pressures that stop the penetration of arterial blood past the applied cuff for surgical time periods which can extend from a few minutes to several hours. Tourniquet cuffs of the prior art differ substantially from pneumatic cuffs designed and used for other purposes. For example, pneumatic cuffs employed in the intermittent measurement of blood pressure are typically designed to apply much lower pressures for much shorter periods of time to selected arteries beneath an inflatable bladder portion of the cuff that does not surround the limb; such cuffs must meet standards of design that are fundamentally different from key design parameters of the safest and most effective tourniquet cuffs. Tourniquet cuffs of the prior art are not designed to serve a sensing purpose, and blood-pressure cuffs of the prior art are not designed to serve an effector purpose.

The inward compressive force applied to a limb by a pressurized tourniquet cuff to close underlying arteries is not equal across the width of the cuff, from proximal to distal edges. Consequently when inflated to a minimum pressure required to stop arterial blood flow past the distal edge of the tourniquet cuff, arterial blood within the limb still penetrates beneath the proximal edge of the cuff for some distance to a location where the arteries become closed. In addition to the pneumatic pressure to which a selected tourniquet cuff is inflated, several variables affect the distance to which arterial blood penetrates beneath the cuff. These variables include: the patient's limb characteristics (for example, limb shape, circumference and soft tissue characteristics at the cuff location); characteristics of the selected tourniquet cuff (for example, cuff design, cuff shape and cuff width); the technique of application of the cuff to the limb (for example, the degree of snugness or looseness of application and the absence, presence and type of underlying limb protection sleeve); physiologic characteristics of the patient including blood pressure and limb temperature; the anesthetic technique employed during surgery (for example, whether a general or regional anesthetic is given, the types and dosages of anesthetic agents employed and the degree of attention paid to anesthetic management); the length of time the tourniquet remains inflated on the limb; changes in limb position during surgery; and any shift in the location of the cuff relative to the limb during surgery.

Many studies published in the medical literature have shown that the safest tourniquet pressure is the lowest pressure that will stop the penetration of arterial blood past a specific cuff applied to a specific patient for the duration of that patient's surgery. Such studies have shown that higher tourniquet pressures are associated with higher risks of tourniquet-related injuries to the patient. Therefore, when a tourniquet is used in surgery, surgical staff generally try to use the lowest tourniquet pressure that in their judgment is safely possible.

It is well established in the medical literature that the optimal guideline for setting the pressure of a constant-pressure tourniquet is based on "Limb Occlusion Pressure" (LOP). LOP can be defined as the minimum pressure required, at a specific time in a specific tourniquet cuff applied to a specific patient's limb at a specific location, to stop the flow of arterial blood into the limb distal to the cuff. LOP is affected by variables including the patient's limb characteristics, characteristics of the selected tourniquet cuff, the technique of application of the cuff to the limb, physiologic characteristics of the patient including blood pressure and limb temperature, and other clinical factors (for example, the extent of any elevation of the limb during LOP measurement and the extent of any limb movement during measurement). The currently established guideline for setting tourniquet pressure based on LOP is that an additional safety margin of pressure is added to the measured LOP, in an effort to account for variations in physiologic characteristics and other changes that may be anticipated to occur normally over the duration of a surgical procedure.

Some surgical tourniquet systems of the prior art include means to measure LOP automatically. Prior-art tourniquet apparatus having automatic LOP measurement means are described by McEwen in U.S. Pat. No. 5,439,477 and by McEwen and Jameson in U.S. Pat. No. 5,556,415. Such prior-art systems have included blood flow transducers that employ a photoplethysmographic principle to sense blood flow in the distal limb, although other transducers have been suggested in the prior art to measure blood flow based on other principles. A blood flow transducer employing the photoplethysmographic principle uses light to indicate the volume of blood present in a transduced region, consisting of a combination of a residual blood volume and a changing blood volume resulting from arterial pulsations. An additional predetermined pressure margin based on recommendations in published surgical literature is added to the automatically measured LOP to provide a "Recommended Tourniquet Pressure" (RTP), as a guideline to help the surgical staff select the lowest tourniquet pressure that will safely stop arterial blood flow for the duration of a surgical procedure. Such prior-art systems allow the surgical staff to select the RTP based on LOP as the tourniquet pressure for that patient, or to select another pressure based on the physician's discretion or the protocol at the institution where the surgery is being performed.

Despite the improved performance of prior-art apparatus that automatically measures LOP, there are three significant limitations. The first limitation is that a separate, complex and costly distal flow sensor is required: the correct application and use of the required distal sensor for automatic LOP measurement is dependent on the skill, training and experience of the surgical staff; the sensor must be located distally on the limb undergoing surgery and this may not be possible in some instances; in other instances the distal location of the sensor requires placement of a non-sterile sensor in or near a sterile surgical field and interferes with the pre-surgical preparation of the limb, thus disrupting the pre-surgical workflow and undesirably increasing the overall perioperative time and costs.

A second limitation is that the apparatus of the prior art does not measure or estimate any changes to LOP that may occur during surgery. The third limitation is that the Recommended Tourniquet Pressure (RTP) is not a personalized tourniquet pressure (PTP) for that individual patient, and instead is a population estimate equaling the sum of the LOP measured at some time pre-surgically plus a population-based and predetermined increment of pressure. This increment is set to be an increment greater than the magnitude of an increase in LOP normally expected during surgery, but the amount of increment is based on aggregated data from a population of surgical patients during a wide variety of surgical procedures and is not personalized to an individual patient undergoing a specific surgical procedure under a specific anesthetic protocol. Accordingly, an RTP of the prior art is not a PTP, and may be higher or lower than optimal.

In U.S. Pat. No. 6,605,103 Hovanes et al. describe apparatus for detecting the flow of blood past a tourniquet cuff and into a surgical field. Such prior-art apparatus is impractical because blood must flow past the tourniquet cuff before it can be detected, requiring surgical staff to do one of two things if blood enters the surgical field: interrupt the surgical procedure and take action to remove the blood; or proceed with blood in the field which might affect visualization and the quality of surgery. Further, Hovanes et al. relies on the accurate sensing of the onset of blood flow past a tourniquet cuff by the measurement of blood flow-related signals. Such apparatus can only be used when arterial blood is actually flowing past the tourniquet cuff toward the surgical field.

Certain prior-art systems adapt ultrasonic Doppler techniques to sense the penetration of arterial blood within a portion of a limb beneath an encircling tourniquet cuff. Examples of such systems are described by McEwen and Jameson in U.S. Pat. No. 8,366,740 and US Patent Publication No. 2013/0144330, and by McEwen et al in US Patent Publication No. 2013/0190806. Detection of arterial blood penetration within a limb beneath a tourniquet cuff by adapting ultrasonic Doppler apparatus and methods requires the accurate measurement of small pulsatile signals in the presence of relatively large levels of noise, especially as the amount of arterial blood beneath the cuff decreases. Further, detection of blood penetration by such methods must be rapid as well as accurate, to facilitate dynamic and accurate control of tourniquet pressure during surgery. Ultrasonic tourniquet systems of the prior art have other significant limitations: the additional ultrasonic sensing arrays required, together with the associated ultrasonic signal processing circuitry and software, are costly; also, adapting and incorporating ultrasonic sensing arrays into tourniquet cuffs is complex and costly, and may be prohibitive in view of the fact that competing tourniquet systems employ cuffs that are sterile, low-cost, disposable products; further, the safe operation of ultrasonic tourniquet systems is at present complex and user-dependent, requiring additional user training and skill.

Tourniquet systems have also been found to be useful for stopping arterial blood flow past an applied tourniquet cuff for a variety of non-surgical medical procedures. Tourniquet systems may also be used to stop arterial blood flow past an applied cuff applied at regions of a patient other than on the patient's arm or leg. For example, occluding arterial bloodflow to the scalp can be beneficial for reducing chemotherapy-related alopecia, and occluding arterial bloodflow to the hand and foot may be beneficial for reducing nail loss and 'hand-foot syndrome' resulting from chemotherapy. Thus, when characterizing the minimum pressure required in a cuff to prevent arterial blood flow past the cuff, the more general term Distal Occlusion Pressure (DOP) is used instead of LOP.

There is a need for a tourniquet system that can establish and maintain a tourniquet pressure that is personalized for each patient, and optimized for each surgical or medical procedure, and for each applied tourniquet cuff. Preferably, such a system would be implemented without the need for substantially increased training, knowledge or skill on the part of the medical staff. There is also a need for a personalized tourniquet system that overcomes the requirement of the prior art for a separate, complex and costly distal blood flow sensor or other apparatus for estimating the patient's limb or distal occlusion pressure before a surgical or medical procedure. Such a system would also overcome the requirement of the prior art for separate, costly and complex apparatus to sense, display, monitor and control the distance of penetration of arterial blood beneath an applied tourniquet cuff. There is a related need for a personalized tourniquet system having a dual-purpose tourniquet cuff wherein the same inflatable bladder of the tourniquet cuff can be separately operated as a patient sensor or as a tourniquet effector, or simultaneously operated as a combined sensor and effector.

BRIEF DESCRIPTION OF THE DRAWINGS

FIGS. 6a, 6b, 6c, 7a, 7b, 8a and 8b show graphical icons that depict changes in distance of penetration and corresponding physiologic pulsations and reference pulsations.

DETAILED DESCRIPTION OF PREFERRED EMBODIMENTS

The embodiments illustrated are not intended to be exhaustive or limit the invention to the precise form disclosed. They are chosen and described in order to explain the principles of the invention and its application and practical use, and thereby enable others skilled in the art to utilize the invention.

Figure 1:
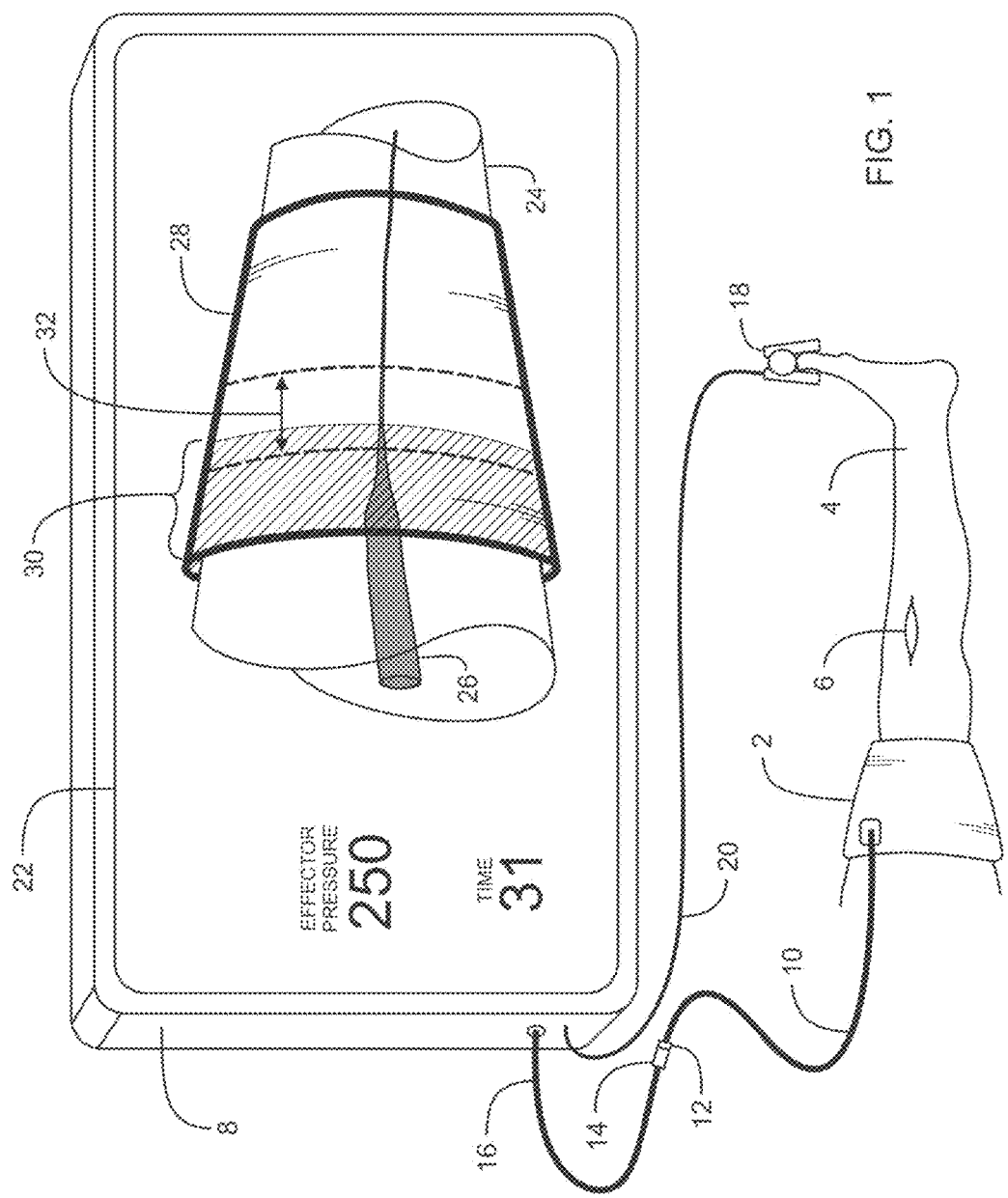
FIG. 1 is a pictorial representation of a preferred embodiment in use during surgery.

FIG. 1 depicts the tourniquet system of a preferred embodiment in clinical use for a surgery on a limb or other patient extremity. Tourniquet cuff 2 is shown encircling a patient limb 4 at a location proximal to surgical site 6 and pneumatically connected to instrument 8. Cuff 2 is a dual-purpose tourniquet cuff that effects the stoppage of blood penetration past the cuff when inflated and senses changes in blood penetration in the portion of the limb encircled by the cuff when blood penetration past the cuff is stopped.

Cuff 2 is a type of tourniquet cuff that has common predetermined parameters that makes it suitable as a dual-purpose cuff including: a single inflatable bladder having a length sufficient to surround a region of a patient at a predetermined location; a cuff width-to-circumference ratio that is substantially different than other types of cuffs such as those approved for blood pressure measurement; a continuous pneumatic passageway that pneumatically connects a cuff port 10 to all parts of the inflatable bladder; and construction, materials, fasteners and design that produce safe low-pressure gradients on tissues beneath cuff 2 when cuff 2 is inflated to a level that prevents penetration of arterial blood past cuff 2 for the duration of a surgical or medical procedure.

A pneumatic passageway between instrument 8 and cuff 2 is provided by cuff port 10, male locking connector 12, female locking connector 14 and flexible tubing 16. Cuff port 10 is of sufficient length to allow a pneumatic connection to cuff 2 to be made outside of a sterile surgical field. Cuff port 10 is fitted with a male locking connector 12 that mates to form a releasable pneumatic connection with female locking connector 14.

To permit instrument 8 to automatically determine if cuff 2 is acceptable for the dual purposes of sensing blood penetration and effecting the stoppage of blood penetration past the cuff, male locking connector 12 includes indicia that identify the physical characteristics of cuff 2. In the preferred embodiments the indicia is a distinct color that identifies the distinct physical characteristics of cuff 2 to instrument 8 and to a user of the preferred embodiments.

Female locking connector 14 includes a sensor responsive to the color of connector 12 and communicates the detected color information to instrument 8 when male connector 12 is mated with connector 14 to form a pneumatic passageway. It will be appreciated that alternate methods of automatically identifying cuff 2 may be used, for example: incorporating RFID devices into cuff 2 or into connector 12, or configuring the shape of connectors 12 and 14 so that only dual-purpose cuffs are connectable to instrument 8.

The preferred embodiment shown in FIG. 1 includes a distal blood transducer 18 which is shown adapted to be applied to a portion of limb 4 distal to cuff 2 and connected to instrument 8 by cable 20. Blood transducer 18 is similar in function and construction to the transducer described in U.S. Pat. No. 8,425,426. In a preferred embodiment blood transducer 18 is used to automatically determine the Distal Occlusion Pressure (DOP) at a time prior to the commencement of a surgical or medical procedure when blood penetration past the cuff is permitted and will not interfere with performance of the procedure. The DOP is the minimum level of pressure required in the inflatable bladder of cuff 2 to stop arterial blood from penetrating past the region of a patient encircled by cuff 2, i.e., in a direction toward a patient extremity. The DOP is used by the preferred embodiments as described further below to establish a Personalized Tourniquet Pressure (PTP). A PTP is a patient-specific safe level of pressure greater than DOP to be maintained in the inflatable bladder of cuff 2 during the period of time that the surgical or medical procedure is being performed.

Instrument 8 utilizes a graphical touchscreen user interface 22 to display information to the user and to permit the user to control the operation of the preferred embodiments.

A user of the preferred embodiments may initiate or confirm desired actions to be performed by instrument 8 by touching touchscreen 22 within the perimeter of a graphical icon representative of an action to be performed by instrument 8. For example: a user may: during the pre-surgical time period select to operate cuff 2 as a patient sensor to estimate a Personalized Tourniquet Pressure (PTP); select to operate cuff 2 as an effector to maintain a level of pressure near the estimated PTP in cuff 2 during surgery; adjust the level of pressure maintained in cuff 2; initiate the pressurization of cuff 2; initiate the depressurization of cuff 2 to a pressure level near zero; set a time limit for a procedure time alarm; temporarily silence audible alarms; and set other operational parameters of instrument 8. A user may be selectively inhibited from initiating some actions when hazard conditions are detected. Some operations may require the user to complete confirmation steps prior to initiating the desired action.

Touchscreen user interface 22 also displays information pertaining to the operation of instrument 8 to the user. Touchscreen user interface 22 may selectively display any of the following information: the level of pressure within cuff 2 measured by instrument 8 (effector pressure); the pressure level to be maintained in cuff 2 when cuff 2 is inflated (reference pressure level); the length of time that cuff 2 has been inflated (procedure time); pressure warning indicators; alarm reference "limits" or values; alarm messages describing detected alarm events; icons indicative of blood penetration past the cuff while blood flow past the cuff is stopped; and other information and instructions pertinent to the operation of instrument 8. To facilitate a clear and rapid understanding of the information presented to the user of instrument 8, alphanumeric text, graphic icons, and color may all be used to convey information.

In FIG. 1 touchscreen user interface 22 is shown during the procedure time period after a Personalized Tourniquet Pressure has been established. A pictorial representation of blood penetration into the region of a patient encircled by cuff 2 is displayed by touchscreen 22. The pictorial representation of blood penetration shown in FIG. 1 consists of: limb segment icon 24, artery icon 26, cuff icon 28, a distance of penetration indicator 30 that indicates the distance of penetration of arterial blood into the region of the limb encircled by cuff 2; and a safety margin indicator 32.

The distance of penetration of arterial blood varies over each cardiac cycle, for simplicity, in describing the present invention; the term 'distance of penetration' is used to refer to the maximum distance of penetration during a cardiac cycle.

As described further below the pictorial representation of blood penetration past the cuff into the region of the limb encircled by cuff 2 is continually updated during the procedure time period so that the distal edge of indicator 30 and the shape of artery icon 26 represent the current distance of penetration as determined by the preferred embodiments.

Figure 2:
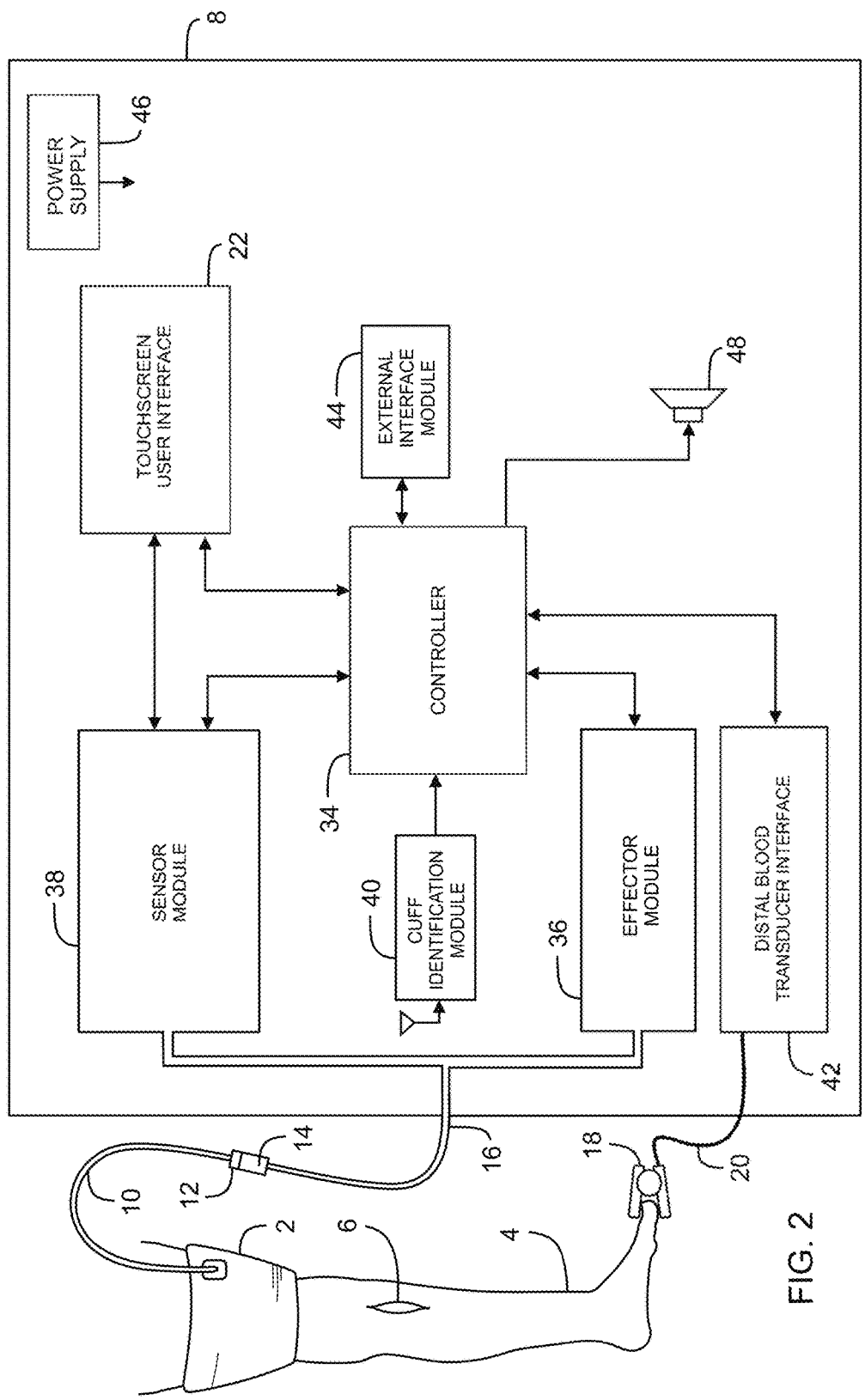
FIG. 2 is a block diagram of a preferred embodiment.

A block diagram of a preferred embodiment of instrument 8 is shown in FIG. 2. Referring to FIG. 2, controller 34 is a microcontroller typical of those known in the art with associated memory, analog, and digital peripheral interface circuitry, and other support components. Controller 34 executes software programs that control the operation of instrument 8 as described below. For clarity, and to enable a better understanding of the principles of the invention, some functions that are performed by controller 34 in conjunction with actuators and transducers are described and shown in FIG. 2 as separate functional blocks. These function blocks include effector module 36, sensor module 38, cuff identification module 40, distal blood transducer interface 42 and external interface module 44.

Power supply 46 connects to an external AC supply and provides regulated DC power for the normal operation of all electronic components of instrument 8. Power supply 46 also includes a battery to enable instrument 8 to continue to operate for a period of time in the absence of an external AC supply.

Speaker 48 is used to alert a user of the preferred embodiments to alarm conditions. Speaker 48 is connected to controller 34. Electrical signals having different frequencies to specify different alarm signals and conditions are produced by controller 34 and converted to audible sound by speaker 48.

Instrument 8 may communicate with an external operating room information system or other external device via external interface module 44. External interface module 44 provides the physical communication interface such as USB, Ethernet, Bluetooth or Wi-Fi and the appropriate communication protocol specific to the connected external device. Data that may be reported to an external device includes: data and events occurring prior to the commencement of a surgical or medical procedure such as the measurement of the minimum pressure required to stop blood penetration past cuff 2, cuff pressure level settings, and alarm limit settings; data and events occurring during a procedure such as: alarm conditions, distances of blood penetration, cuff pressure levels, adjustments to pressure level settings and alarm limit settings.

Cuff identification module 40 communicates wirelessly with color sensors that form part of female connector 14. When cuff connector 12 is mated with connector 14, color sensors within connector 14 determine the color of connector 12. The color information from the sensors is communicated to cuff identification module 40.

Cuff identification module 40 maintains a data table that associates cuff connector color with predetermined physical characteristics of the connected cuff. The characteristics of the connected cuff are communicated to controller 34 and used by controller 34 as described further below. An example of a data table maintained by cuff identification module is shown below in Table 1.

TABLE 1

| Connector Color | Dual-Purpose Cuff | Bladder Shape | Bladder Width | Bladder Length |
|---|---|---|---|---|
| Red | Yes | Curved | 3.25 in. | 18 in. |
| Green | Yes | Curved | 3.5 in. | 24 in. |
| Blue | Yes | Curved | 3.5 in. | 34 in. |
| Purple | Yes | Rectangular | 3.75 in. | 44 in. |

TABLE 1-continued

| Connector Color | Dual-Purpose Cuff | Bladder Shape | Bladder Width | Bladder Length |
|---|---|---|---|---|
| Yellow | Yes | Rectangular | 1.5 in. | 44 in. |
| White | No | unknown | unknown | unknown |

If the type of cuff connected to instrument 8 is not a dual-purpose cuff, controller 34 alerts the user of instrument 8 by displaying a warning message on touchscreen 22 and configures touchscreen 22 to inhibit the selection of the cuff to operate as a sensor and effector. Touchscreen 22 may also be configured to permit a user to override the inhibited selection and permit the cuff to operate as an effector.

Touch screen user interface 22 is similar to the touchscreen user interface described in U.S. Pat. App. No. 20130211445 and includes features to prevent hazards and suppress inadvertent and unintended actions. Touchscreen user interface 22 communicates with controller 34 to initiate actions and receive data for display. Touch screen user interface 22 also receives distance of penetration data from sensor module 38 to display in a pictorial representation as shown in FIG. 1.

Blood transducer interface module 42 communicates with blood transducer 18 via cable 20 and with controller 34. Blood transducer 18 employs the principle of photoplethysmography and responds to arterial blood that penetrates past cuff 2. Blood transducer interface module 42 processes the signals from transducer 18 and produces an indication to controller 34 when blood is penetrating past cuff 2. Prior to the commencement of the surgical or medical procedure, to determine the minimum pressure level required in the inflatable bladder of cuff 2 to stop blood penetration past cuff 2 (DOP) controller 34 operates to incrementally increase the pressure in the inflatable bladder of cuff 2 until blood transducer interface module 42 no longer indicates that blood is penetrating past cuff 2. The pressure level in the inflatable bladder of cuff 2 when blood penetration past cuff 2 is no longer detected is the minimum pressure level required to stop blood penetration past cuff 2.

Figure 3:
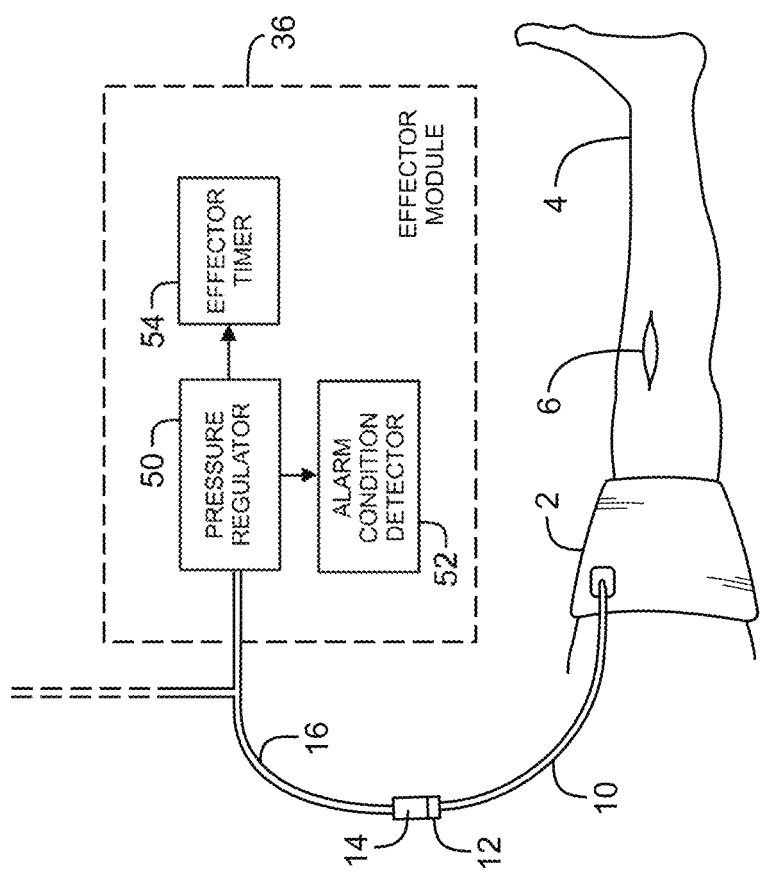
FIG. 3 is a detailed block diagram of the effector module.

Effector module 36 communicates with controller 34 and communicates pneumatically with the inflatable bladder of cuff 2. Effector module 36 is shown in detail in FIG. 3. Referring to FIG. 3, effector module 36 includes a pressure regulator 50, an alarm condition detector 52 and an effector timer 54. Pressure regulator 50 is an assemblage of components for regulating the pressure of air in the inflatable bladder of cuff 2 near a reference pressure level communicated from controller 34. Pressure regulator 50 is similar in design and operation to the tourniquet pressure regulator described in U.S. Pat. No. 8,083,763 and includes a combination of valves and a pressure source for maintaining the pressure level within the inflatable bladder of cuff 2 near a reference pressure level.

During a procedure when cuff 2 is inflated to stop penetration of blood past cuff 2, alarm condition detector 52 monitors the operation of pressure regulator 50 and communicates signals indicative of detected alarm conditions to controller 34. Alarm conditions detected by alarm condition detector 52 are: occlusion of the pneumatic passageway between pressure regulator 50 and the inflatable bladder of cuff 2 (occlusion alarm); leakage from the inflatable bladder of cuff 2 or the pneumatic passageway between pressure regulator 50 and the inflatable bladder of cuff 2 (leak alarm); bladder pressure level too far below the desired reference pressure level (low pressure alarm); bladder pressure level too far above the desired reference pressure level (high pressure alarm); malfunction of pressure regulator 50 (malfunction alarm). It will be appreciated that other alarm conditions relevant to the operation of pressure regulator 50 may be detected by alarm condition detector 52.

Effector timer 54 operates to produce an indication of the length of time in minutes that the inflatable bladder of cuff 2 has been inflated (procedure time). The procedure time is communicated to controller 34 and displayed on touchscreen 22 when cuff 2 is operating as an effector to prevent blood from penetrating past cuff 2.

Referring to FIG. 2, sensor module 38 communicates pneumatically with the inflatable bladder of cuff 2 and communicates with controller 34 and touchscreen user interface 22. Sensor module 38 senses and analyzes pneumatic pulsations occurring in the inflatable bladder of cuff 2 to establish a Personalized Tourniquet Pressure (PTP) and to produce an ongoing estimate of the distance of penetration of arterial blood into the region encircled by cuff 2 while blood penetration past cuff 2 is stopped.

The sensed pneumatic pulsations primarily arise from volume changes in the region of a patient encircled by cuff 2, and those volume changes are produced by the penetration of arterial blood during each cardiac cycle into, but not past, the region encircled by cuff 2 while the inflatable bladder of cuff 2 is inflated to a level that stops the penetration of blood past cuff 2. As noted above for simplicity, in describing the present invention, the term 'distance of penetration' is used to refer to the maximum distance of penetration during a cardiac cycle.

Figure 4:
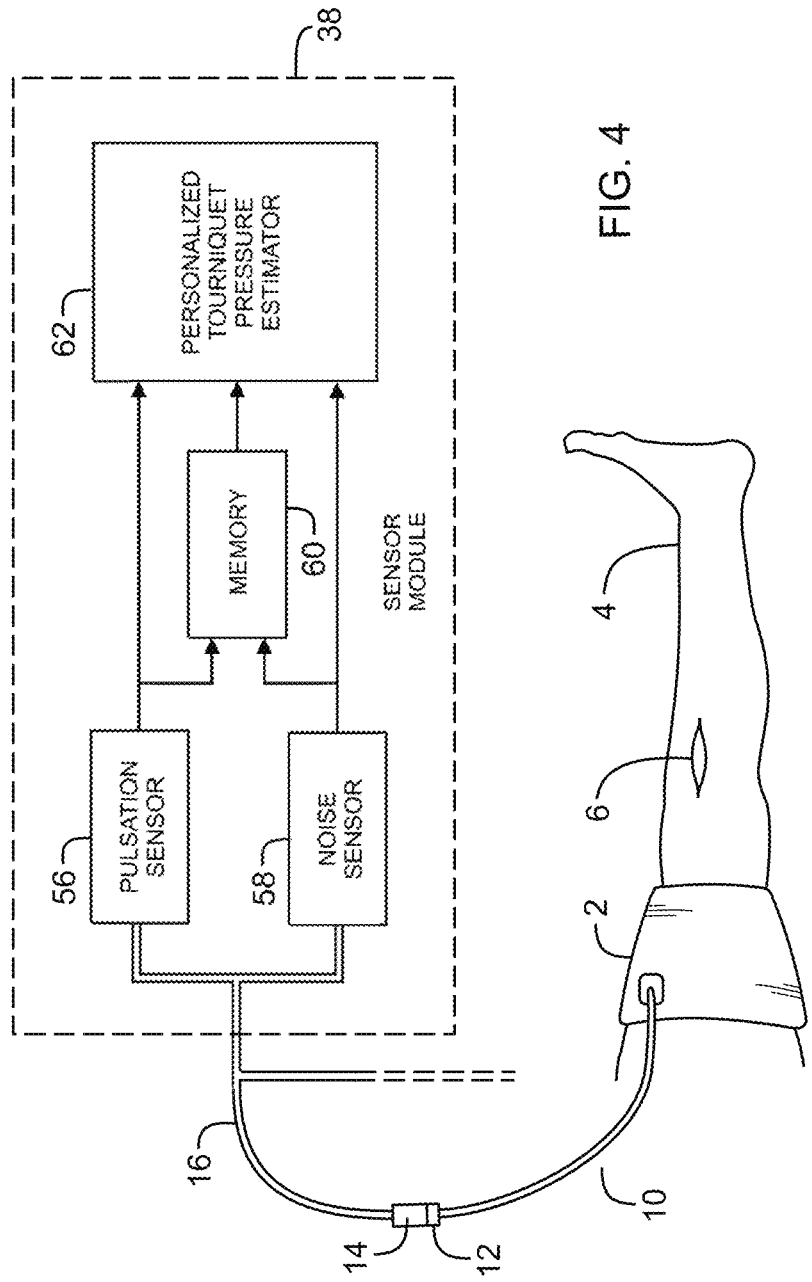
FIG. 4 is detailed block diagram of the sensor module.

Sensor module 38 is shown in detail in FIG. 4. Referring to FIG. 4, pulsation sensor 56 is shown in pneumatic communication with the inflatable bladder of cuff 2. Pulsation sensor 56 is optimized to detect and characterize pneumatic pulsations that are physiologic in origin and correspond to blood penetration into the region of a patient encircled by cuff 2 occurring during each cardiac cycle. Levels of pulsation characteristics produced by sensor 56 that are indicative of differing distances of penetration include maximum pulsation amplitude, pulsation area (integral over a cardiac cycle), and pulsation frequency spectrum. It will be appreciated that other pulsation characteristics may also be produced by sensor 56.

Sources of noise unique to the perioperative environment that the preferred embodiments are used in, may produce pressure fluctuations in the bladder of cuff 2 that are independent of the pneumatic pulsations corresponding to the penetration of blood into the region of a patient encircled by cuff 2. Some of these noise sources can produce pressure fluctuations that mimic physiologic pulsations associated with blood penetration and effect the accuracy of the levels of pulsation characteristics produced by pulsation sensor 56. To characterize and quantify the level of noise present while physiologic pressure pulsations are being sensed by pulsation sensor 56 and to better discriminate between physiologic pressure pulsations and pressure fluctuations caused by noise sources and to help ensure accurate characterization of pulsations the preferred embodiments include noise sensor 58. Noise sensor 58 communicates pneumatically with the bladder of cuff 2.

Figure 5A:
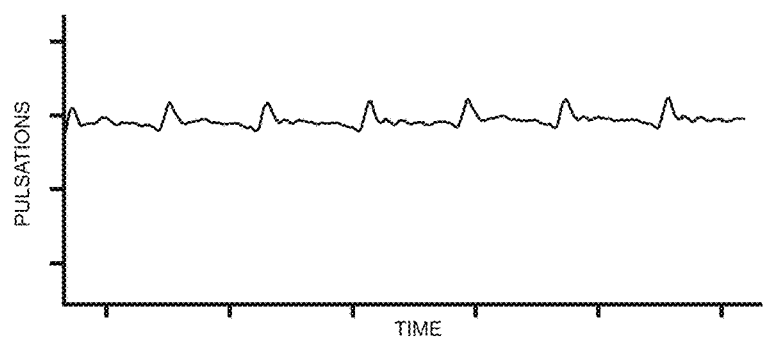
FIGS. 5a, 5b, 5c, and 5d are graphs of pneumatic pulsations and noise sensed by the dual-purpose cuff.
Figure 5B:
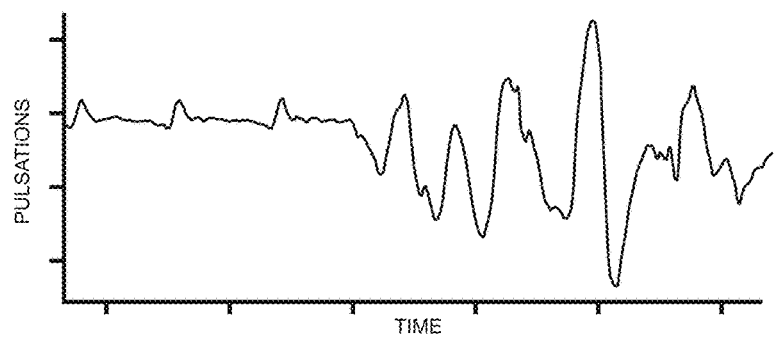
Figure 5C:
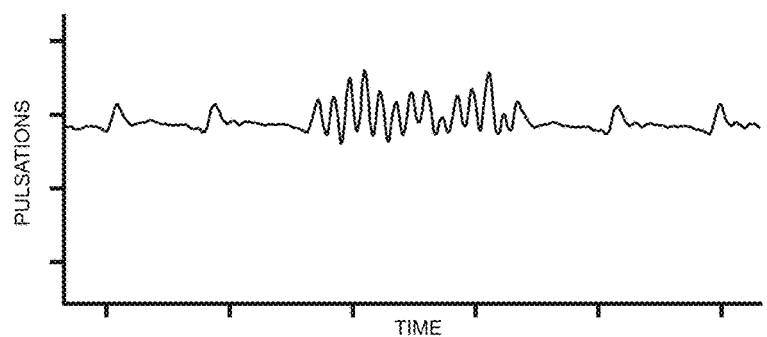
Figure 5D:
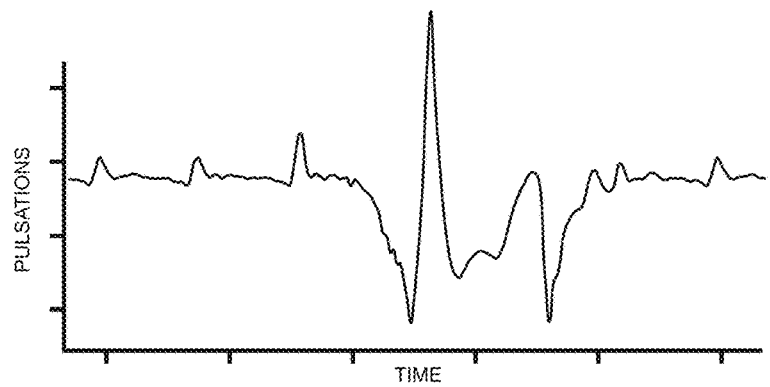

Examples of physiologic pneumatic pulsations and pressure fluctuations caused by various noise sources are shown in FIGS. 5a, 5b, 5c and 5d. FIG. 5a is a graphical representation of physiologic pneumatic pulsations in the absence of noise sources. FIG. 5b is a graphical representation of physiologic pneumatic pulsations and pulsations produced by movement of limb 4. FIG. 5c is a graphical representation of physiologic pneumatic pulsations and pulsations produced by shivering of the patient. FIG. 5d is a graphical representation of physiologic pneumatic pulsations and pulsations produced by the normal operation of pressure regulator 50.

Information relating to the physical characteristics of cuff 2 from cuff identification module 40 may be used by physiologic pulsation sensor 56 and noise sensor 58 to better optimize the sensing of physiologic pulsations and to better determine levels of noise.

The levels of characteristics of each sensed physiologic pulsation are communicated to pulsation memory 60 and to personalized tourniquet pressure estimator 62 by pulsation sensor 56. The level of noise associated with the sensed pulsation is also communicated to memory 60 and estimator 62 by noise sensor 58. If the level of noise associated with a sensed pulsation exceeds a predetermined threshold the levels of the pulsation's characteristics may be rejected by memory 60 and estimator 62. If the number of rejected pulsations exceed a predetermined alert limit within a predetermined alert time period, controller 34 acts to signal the user by displaying an alarm message on touchscreen 22 and producing an audio tone.

For a sensed pulsation, memory 60 records the levels of pulsation's characteristics, the level of noise near the time the pulsation was sensed and the level of pressure in the bladder of cuff 2 near the time when the pulsation was sensed. Pulsation memory 60 may record the levels of pulsation characteristics and associated level of noise and associated level of pressure in the bladder of cuff 2 for one or more sensed pulsations depending on the operating mode of the preferred embodiments.

In the preferred embodiments personalized tourniquet pressure estimator 62 is used to: estimate a Personalized Tourniquet Pressure (PTP), produce ongoing estimates of distance of penetration during the procedure time period, and establish a margin of safety for the distance of penetration estimates.

During the period of time prior to the commencement of the surgical or medical procedure a user of the preferred embodiments may initiate an estimate of PTP via touchscreen user interface 22. If cuff identification module 40 does not detect an acceptable dual-purpose cuff pneumatically connected to instrument 8, touchscreen 22 inhibits the initiation of an estimate of PTP.

To establish a Personalized Tourniquet Pressure (PTP) to be maintained during the procedure time period, controller 34, sensor module 38 and estimator 62 operate in a preferred embodiment as described in the following sequence:

a) Distal Occlusion Pressure (DOP) is first estimated as described above using blood transducer 18, controller 34 then directs effector module 36 to inflate the bladder of cuff 2 to the DOP level.

b) While the level of pressure in the bladder of cuff 2 is near the DOP the levels of physiologic pulsation characteristics associated with the DOP are recorded in pulsation memory 60, these levels of pulsation characteristics associated with DOP are representative of the maximum distance of penetration of blood into the region of a patient encircled by cuff 2 while blood penetration completely past cuff 2 is stopped.

c) To determine a Personalized Tourniquet Pressure (PTP) level that is greater than DOP and results in a distance of penetration that is less than the maximum distance, estimator 62 retrieves from memory 60 the levels of pulsation characteristics associated with DOP and computes using predetermined percentages the levels of pulsation characteristics that will correspond to levels of pulsation characteristics detected when the bladder of cuff 2 is at a level of pressure near the PTP.

d) Controller 34 next directs effector module 36 to incrementally increase the level of pressure in the bladder of cuff 2 while estimator 62 compares the levels of detected pulsation characteristics with the levels of the previously computed pulsation characteristics corresponding to the PTP. When the levels of characteristics of detected pulsations are near the levels of the computed pulsation characteristics the level of pressure in the bladder of cuff 2 is near the PTP and controller 34 ceases to increment the pressure level in the bladder of cuff 2. The level of pressure in the bladder of cuff 2 is recorded by controller 34 as the estimated PTP.

It will be appreciated that controller 34 may also determine the PTP by increasing the level of pressure in the bladder of cuff 2 to level substantially greater than the DOP and then incrementally reducing the level of pressure in the bladder of cuff 2 until the levels of detected pulsation characteristics are near the levels of the previously computed pulsation characteristics corresponding to the PTP.

When the estimate of PTP is completed, the estimated PTP recorded by controller 34 is displayed on touchscreen user interface 22, and a user may then select the PTP as the level of pressure to be maintained in the bladder of cuff 2 during the procedure time period.

The predetermined percentages used by estimator 62 to compute pulsation characteristics corresponding to the PTP may be a function of the measured DOP. The predetermined pulsation percentages used by estimator 62 may also be dependent upon the characteristics of cuff 2 as reported by cuff identification module 40. For example, if the measured DOP is less than 140 mmHg a percentage of 50% may be used, if the DOP is greater or equal to 140 mmHg a percentage of 55% may be used or if the cuff has a length greater than 34 inches a percentage of 60% may be used.

Pulsation characteristics used by estimator 62 in determining a PTP may include one or a combination of maximum pulsation amplitude, pulsation shape, pulsation area (integral) and pulsation frequency spectrum.

To estimate PTP when an estimate of DOP is not available sensor module 38 may be configured to analyze the pneumatic physiologic pulsations in the bladder of cuff 2 as follows:

a) Controller 34 directs effector module 36 to inflate the bladder of cuff 2 to a predetermined default pressure level chosen to stop the penetration of blood past the region of a patient encircled by cuff 2 and to produce a distance of penetration that is minimal. The distance of penetration is minimal when a change in the level of pressure in cuff 2 or a change in patient blood pressure does not produce a significant change in the level of the maximum amplitude of sensed pulsations.

b) The maximum amplitude of the detected physiologic pulsations associated with the default level of pressure in the bladder of cuff 2 are recorded in pulsation memory 60.

c) Estimator 62 then computes as a percentage of the maximum amplitude of pulsations associated with the default level of pressure the maximum amplitude of a reference pulsation associated with a level of pressure lower than the default level.

d) Controller 34 then directs effector module 36 to decrease the level of pressure in the bladder of cuff 2 by predetermined increments until physiologic pulsations with a maximum amplitude level near the computed maximum amplitude of the reference pulsation are detected.

e) Estimator 62 computes as a percentage of the maximum amplitude of the reference pulsation the maximum amplitude of pulsations associated with the PTP.

f) Controller 34 then directs effector module 36 to further decrease the level of pressure in the bladder of cuff 2 by predetermined increments until physiologic pulsations in the bladder of cuff 2 with a maximum amplitude near the maximum amplitude of pulsations associated with the PTP are detected. The level of pressure in the bladder of cuff 2 is recorded by controller 34 as the estimated PTP.

Estimator 62 also computes a distance of penetration margin of safety. The margin of safety has upper and lower limits in which the estimated distance of penetration is to be maintained.

Levels of pulsation characteristics associated with the upper and lower limits of the margin of safety are predetermined percentage of the levels of pulsation characteristics associated with the PTP and are computed by estimator 62.

If the distance of penetration exceeds the upper limit of the margin of safety, too little pressure is being applied by cuff 2 and blood may penetrate past cuff 2. If the distance of penetration exceeds the lower limit more pressure than necessary is being applied by cuff 2 which increases the risk of damage to tissues that are encircled by cuff 2.

To permit a better understanding of how controller 34, sensor module 38 and estimator 62 operate together to use levels of pulsation characteristics to establish a personal tourniquet pressure the following example with sample values for pressure levels, pulsation characteristic levels and ratios is provided. In this simplified example the maximum pulsation amplitude is the only pulsation characteristic used by estimator 62 in establishing a Personalized Tourniquet Pressure (PTP). Higher levels of maximum pulsation amplitude are associated with greater distances of penetration. Prior to the commencement of a surgical or medical procedure cuff 2 and blood transducer 18 are applied to the patient, a measurement of Distal Occlusion Pressure is performed and the DOP is estimated to be 150 mmHg. Cuff 2 is then inflated to 150 mmHg and the physiologic pulsations sensed by pulsation sensor 56 are found to have a maximum amplitude of 4 mmHg. For the DOP of 150 mmHg, estimator 62 selects a predetermined percentage of 60% and calculates the maximum amplitude of pulsations occurring at the Personalized Tourniquet Pressure to be 2.4 mmHg (4*0.6). The level of pressure in cuff 2 is increased until physiologic pulsations having a maximum amplitude near 2.4 mmHg are detected. The level of pressure in cuff 2 when pulsations with a maximum amplitude near 2.4 mmHg are detected is 195 mmHg. 195 mmHg is the Personalized Tourniquet Pressure that is to be maintained in cuff 2 during the procedure time period. Estimator 62 also computes upper and lower distance of penetration safety margin limits based on the maximum amplitude of the pulsations at the PTP, in this example estimator 62 uses a percentage 120% for the upper limit and 70% for the lower limit, for maximum pulsation amplitudes of 2.88 mmHg (2.4*1.2) and 1.68 mmHg (2.4*0.7) respectively.

During the procedure time period when instrument 8 is maintaining the level of pressure in the bladder of cuff 2 near the Personalized Tourniquet Pressure estimator 62 operates to produce an estimate of the distance of penetration of arterial blood past cuff 2 when blood penetration past cuff 2 is stopped. Estimator 62 produces this estimate by comparing the levels of pulsation characteristics of the most recently detected physiologic pulsation with the levels of characteristics of a reference pulsation recorded in pulsation memory 60. The levels of characteristics of the reference pulsation typically correspond to a pulsation occurring when the level of pressure in cuff 2 is near the DOP, however it will be appreciated that levels of characteristics of pulsations occurring at other levels of pressure in cuff 2 may be used.

The distance of penetration estimate is communicated to touchscreen 22 for display to a user. As described above the preferred embodiments display a pictorial representation of distance of penetration estimates to better convey this information to a user. FIGS. 6a, 6b, and 6c show touchscreen 22 displaying pictorial representations of distance of penetration and corresponding graphs of associated physiologic pulsations and reference pulsations at various times throughout the procedure time period while the level of pressure in the bladder of cuff 2 is constant. As shown in FIGS. 6a, 6b, and 6c the level of pressure in the bladder of cuff 2 remains constant.

In FIG. 6a the distal edge of distance of penetration indictor 30 and the shape of artery icon 24 indicate that the distance of penetration is at a nominal distance. The proximal edge of distance of penetration indictor 30 lies within the safety margin limits and they are not being exceeded. The corresponding graph shows a reference physiologic pulsation 602 and the physiologic pulsation 604 associated with the pictorial representation of distance of penetration.

FIG. 6b is illustrative of a decrease in the distance of penetration caused by a decrease in the blood pressure of the patient. The distal edge of penetration indicator 30 lies outside the lower safety margin limit, alarm indicator icon 64 is displayed to alert the user that the safety margin limits have been exceed. The corresponding graph shows reference pulsation 602 and the physiologic pulsation 606 associated with the pictorial representation of distance of penetration. Note that the amplitude of associated physiologic pulsation 606 is less than the amplitude of the reference pulsation 602, indicative of a decrease in the distance of penetration.

FIG. 6c is illustrative of an increase in the distance of penetration caused by an increase in the blood pressure of the patient. The distal edge of penetration indicator 30 lies outside the upper safety margin limit, alarm indicator icon 64 is displayed to alert the user that the safety margin limits have been exceed. The corresponding graph shows reference pulsation 602 and the physiologic pulsation 608 associated with the pictorial representation of distance of penetration. Note that the amplitude of the associated pulsation 608 is greater than the amplitude of the reference pulsation 602, indicative of an increase in the distance of penetration.

FIGS. 7a, 7b, 8a and 8b show touchscreen 22 displaying pictorial representations of distance of penetration and corresponding graphs of associated physiologic pulsations and reference pulsations. These figures illustrate the effect of changing cuff pressure on the distance of penetration.

FIG. 7a is illustrative of a decrease in the distance of penetration caused by a decrease in the blood pressure of the patient. The distal edge of penetration indicator 30 lies outside the lower safety margin limit, alarm icon 64 is displayed to alert the user that the safety margin limits have been exceed. The level of pressure in the bladder of cuff 2 (effector pressure) is 250 mmHg. The corresponding graph shows reference pulsation 702 and the physiologic pulsation 704 associated with the pictorial representation of distance of penetration. Note that the amplitude of associated physiologic pulsation 704 is less than the amplitude of the reference pulsation 702, indicating a decrease the distance of penetration.

FIG. 7b is illustrative of an increase in the distance of penetration caused by a reducing the level of pressure in the bladder of cuff 2. The distal edge of penetration indicator 30 lies within the safety margin limits and alarm icon 64 is not displayed. The level of pressure in the bladder of cuff 2 (effector pressure) has been decreased by a user to 200 mmHg. The corresponding graph shows reference pulsation 702 and the physiologic pulsation 706 associated with the pictorial representation of distance of penetration. Note that the amplitude of associated physiologic pulsation 706 is near the amplitude of the reference pulsation 702, indicating that distance of penetration has been restored to a nominal distance.

Figure 8A:
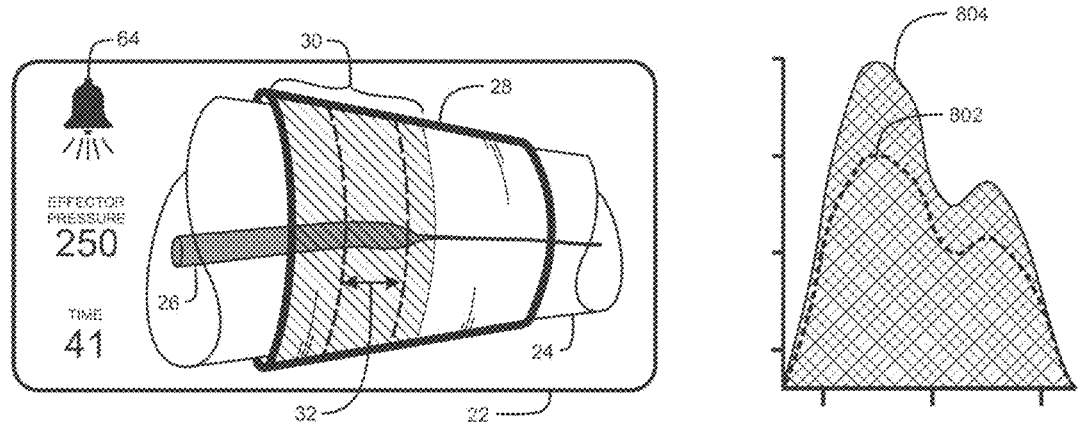

FIG. 8a is illustrative of an increase in the distance of penetration caused by an increase in the blood pressure of the patient. The distal edge of penetration indicator 30 lies outside the upper safety margin limit, alarm icon 64 is displayed to alert the user that the safety margin limits have been exceeded. The level of pressure in the bladder of cuff 2 (effector pressure) is 250 mmHg. The corresponding graph shows reference pulsation 802 and the physiologic pulsation 804 associated with the pictorial representation of distance of penetration. Note that the amplitude of associated physiologic pulsation 804 is greater than the amplitude of the reference pulsation 802, indicating an increase in the distance of penetration.

Figure 8B:
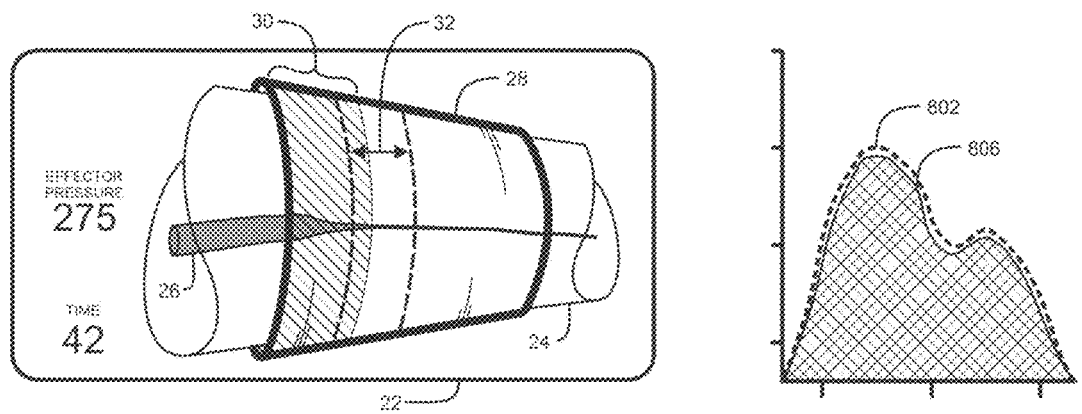

FIG. 8b is illustrative of a decrease in the distance of penetration caused by an increasing the level of pressure in the bladder of cuff 2. The distal edge of penetration indicator 30 lies within the safety margin limits and alarm icon 64 is not displayed. The level of pressure in the bladder of cuff 2 (effector pressure) has been increased by a user to 275 mmHg. The corresponding graph shows reference pulsation 802 and the physiologic pulsation 806 associated with the pictorial representation of distance of penetration. Note that the amplitude of associated physiologic pulsation 806 is near the amplitude of the reference pulsation 802, indicating that distance of penetration has been restored to a nominal distance.

To automatically maintain a safe level of pressure in the inflatable bladder of cuff 2, controller 34 may be configured to regulate the level of pressure in the bladder of cuff 2 to maintain the distance of penetration near a reference level associated with a PTP.

Figure 9:
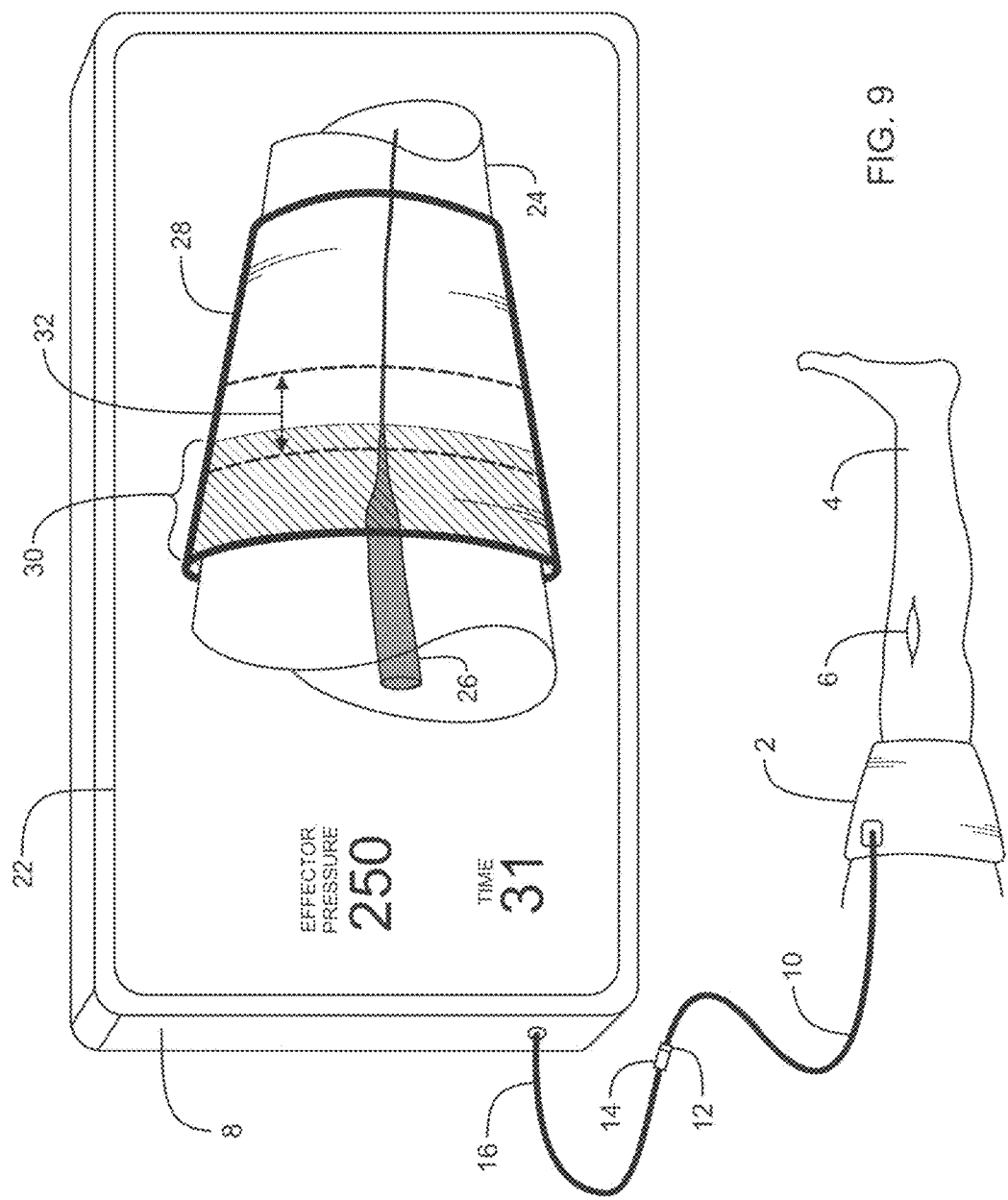
FIG. 9 is a pictorial representation of a second preferred embodiment in use during surgery.
Figure 10:
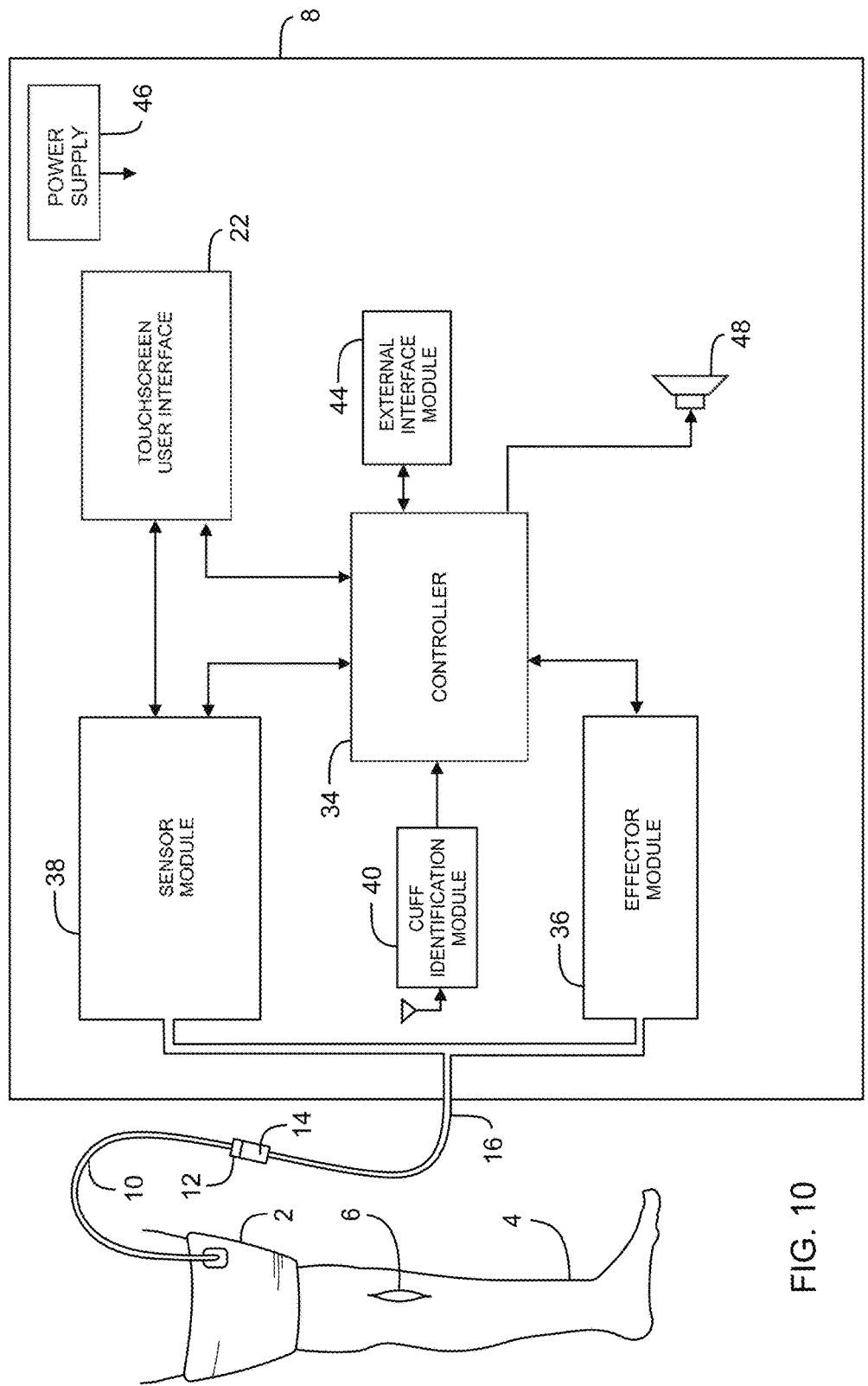
FIG. 10 is a block diagram of the second preferred embodiment.

FIGS. 9 and 10 depict the tourniquet system of a second preferred embodiment. FIG. 9 shows the second preferred embodiment in clinical use and FIG. 10 is a block diagram of this embodiment. This second preferred embodiment is similar to the preferred embodiment described above with the exception that transducer 18 and its related interface do not form part of this embodiment. In the second preferred embodiment described below sensor module 38 performs additional functions to estimate Distal Occlusion Pressure (DOP) directly by using cuff 2 as a sensor and analyzing the levels of characteristics of physiologic pulsations detected at various levels of pressure in the inflatable bladder of cuff 2.

Estimates of DOP and PTP are made during a period of time prior to the commencement of the surgical or medical procedure. When a user initiates an estimate of DOP and PTP via touchscreen interface 22, controller 34 and sensor module 38 operate as follows:

a) Controller 34 directs effector module 36 to inflate the bladder of cuff 2 to a predetermined default pressure level chosen to stop the penetration of blood past the region of a patient encircled by cuff 2 and to produce a distance of penetration that is minimal. In the preferred embodiments the predetermined default pressure level is 300 mmHg. It will be appreciated that other default pressure levels may be predetermined and that the default pressure level may be dependent upon characteristics of the cuff connected to instrument 8 as reported by cuff identification module 40. A default pressure level may also be selected by a user of instrument 8 via touchscreen user interface 22.

b) The levels of characteristics of detected physiologic pulsations associated with the default level of pressure in the bladder of cuff 2 are recorded in pulsation memory 60. The level of noise associated with the detected pulsations is also recorded in pulsation memory 60.

c) Controller 34 then directs effector module 36 to decrease the level of pressure in the bladder of cuff 2 by predetermined increments until a predetermined minimum level of pressure is reached. Following each decrease in the level of pressure in the bladder of cuff 2, the levels of characteristics of detected physiologic pulsations, their associated level of noise and associated level of pressure are recorded in memory 60. When the predetermined minimum level of pressure has been reached controller 34 directs effector module 36 to deflate the bladder.

d) Estimator 62 then retrieves the levels of pulsation characteristics and their associated bladder pressure levels from memory 60. Estimator 62 compares and analyzes the recorded levels of characteristics to determine the maximum levels of pulsation characteristics recorded while the level of pressure in the bladder of cuff 2 was being decreased. Generally, as the level of pressure in the bladder of cuff 2 is decreased the depth of penetration of blood into the region encircled by cuff 2 increases and the levels of characteristics of physiologic pulsations also increase. The levels of characteristics of physiologic pulsations are at their maximum levels when the level of pressure in the bladder of cuff 2 is at a pressure that is below DOP and arterial blood is penetrating past the region of a patient encircled by cuff 2. Levels of characteristics of pulsations associated with DOP have been found to have a predetermined relationship with the maximum levels of pulsation characteristics that are detected when blood is penetrating past the cuff.

e) After determining the maximum levels of pulsation characteristics recorded while the level of pressure in the bladder of cuff 2 was decreased from a default level of pressure to a predetermined minimum level of pressure, estimator 62 computes, using predetermined percentages of the maximum levels the levels of pulsation characteristics that will match the levels of pulsation characteristics detected when the level of pressure in the bladder of cuff 2 is near the DOP.

f) Estimator 62 analyzes the recorded levels of pulsation characteristics and their associated levels of pressure to estimate the patient's DOP by calculating the level of pressure required in the bladder of cuff 2 to produce pulsations with characteristics that match the previously computed levels of pulsation characteristics associated with DOP. Estimator 62 also analyzes the recorded levels of noise associated with the pulsation characteristics to determine the level of noise associated with the DOP estimation. To compensate for any effects that noise may have on the accuracy of the DOP estimation, estimator 62 uses the estimated DOP and the level of noise associated with the DOP estimation to determine the estimated PTP. The estimated PTP computed by estimator 62 is a function of the estimated DOP and the level of noise associated with the DOP estimation. If the level of noise associated with the DOP estimation less than a predetermined low noise threshold, PTP is estimated by adding a predetermined pressure increment to the estimated DOP. If the level noise associated with the DOP estimation is greater than or equal to the low noise threshold and less than a predetermined maximum noise threshold, PTP is estimated by adding a predetermined pressure increment to the estimated DOP that is greater than the predetermined increment added when the level of noise is below the low noise threshold.

If the level of noise associated with the DOP estimation is greater than or equal to predetermined maximum noise threshold level, then PTP cannot be reliably estimated from the estimated DOP and the PTP is set to a predetermined default level, a warning message is displayed on touchscreen 22 and a warning audio tone is produced to alert the user.

For example if the DOP is estimated to be 140 mmHg and the level of noise associated with the estimation is below the low noise threshold the PTP will be estimated to be 190 mmHg (140 mmHg+50 mmHg). If the level of noise is above the low noise threshold and below the maximum threshold the PTP will be estimated to be 215 mmHg (140 mmHg+75 mmHg). If the level of noise is greater than the maximum noise threshold the estimated PTP will be a default pressure of 300 mmHg.

It will be appreciated that other functions of estimated DOP and associated noise levels may be used to estimate a PTP other than the function described above.

It will be apparent that to record the levels of pulsation characteristics associated with varying levels of pressure in the bladder of cuff 2 between a default pressure and a minimum pressure a sequence other than that described above (where the level of pressure is reduced in predetermined amounts from a default level to a minimum level) may be used. For example: controller 34 may direct effector module 36 to inflate the bladder of cuff 2 to a predetermined minimum level and increase the level of pressure in predetermined increments until a default pressure level is reached; controller 34 may also vary the predetermined increment amount, default level of pressure and minimum level of pressure in response to the magnitude of the levels of physiologic pulsation characteristics detected and their associated level of pressure in the bladder of cuff 2.

During the period of time prior to the commencement of a surgical or medical procedure, a user of the second preferred embodiment selects a suitable dual-purpose tourniquet cuff 2 to encircle a region of a patient to which arterial bloodflow past the cuff is to be stopped, for example limb 4 proximal to surgery site 6. The user secures the cuff around the limb and connects it so that the cuff communicates pneumatically with instrument 8. Cuff identification module 40 attempts to identify the cuff to determine if it is an acceptable dual-purpose tourniquet cuff. If the cuff is not an acceptable dual-purpose cuff for use with the preferred embodiment or it cannot be identified a warning is given to the user via touchscreen user interface 22 and the controls employed to initiate an estimate of PTP and to inflate the cuff are disabled, thereby preventing the use of an unacceptable cuff.

If the pneumatically connected cuff is acceptable a user may initiate an estimate of Personalized Tourniquet Pressure (PTP) by touching a corresponding graphic icon shown on touchscreen user interface 22.

To estimate the PTP, instrument 8 will inflate the bladder of cuff 2 to various levels while recording the levels of characteristics of pneumatic physiologic pulsations associated with the pressure levels as described above. During the estimation an icon representing the estimation's progress will be show on touchscreen 22. If during the estimation of PTP, noise that is independent of arterial blood penetration is present, such as noise created by shaving the patient or from the patient shivering, and that noise exceeds a predetermined threshold, the estimation will be suspended and a warning message displayed touchscreen 22.

When instrument 8 has completed an estimation of PTP, the PTP and DOP are displayed on touchscreen 22 and a user may select the estimated PTP as the level of pressure to maintain in the bladder of cuff 2 during the procedure time period. To ensure that the estimated PTP remains relevant to the physiologic state of the patient, controller 34 only permits a user to select the estimated PTP as the level of pressure to be maintained in the bladder of cuff 2 during a procedure for a predetermined period of time after the estimation of PTP has been completed. If the PTP is not selected within the predetermined period of time another estimate of PTP must be initiated or the user must select a default pressure level to be maintained in the bladder of cuff 2 during a procedure.

After selecting the level of pressure to be maintained in the bladder of cuff 2 during the procedure time period the user may initiate the tourniquet effector (inflate cuff 2) by touching an icon on touchscreen 22. If the user has selected the previously estimated PTP as the level of pressure to be maintained in the bladder of cuff 2, instrument 8 will as described above displays icons representing distance of penetration. Sensor module 38 will continually monitor the pneumatic physiologic pulsations arising in the bladder of cuff 2 and display via touchscreen 22 an estimate of the distance arterial blood penetrates into the region of a patient encircled by cuff 2 while the penetration of blood past the cuff is prevented. If the distance of penetration exceeds a predetermined safety margin an alarm message will be shown on touchscreen 22 and an audio tone will be generated to alert the user to the potentially unsafe condition. A user may choose to adjust via touchscreen 22 the level of pressure maintained in the bladder of cuff 2 to restore the distance of penetration to within the margin of safety. A user via touchscreen 22 may configure instrument 8 to automatically adjust the level of pressure within the bladder of cuff 2 to maintain the distance of penetration within the safety margin.

Figure 11:
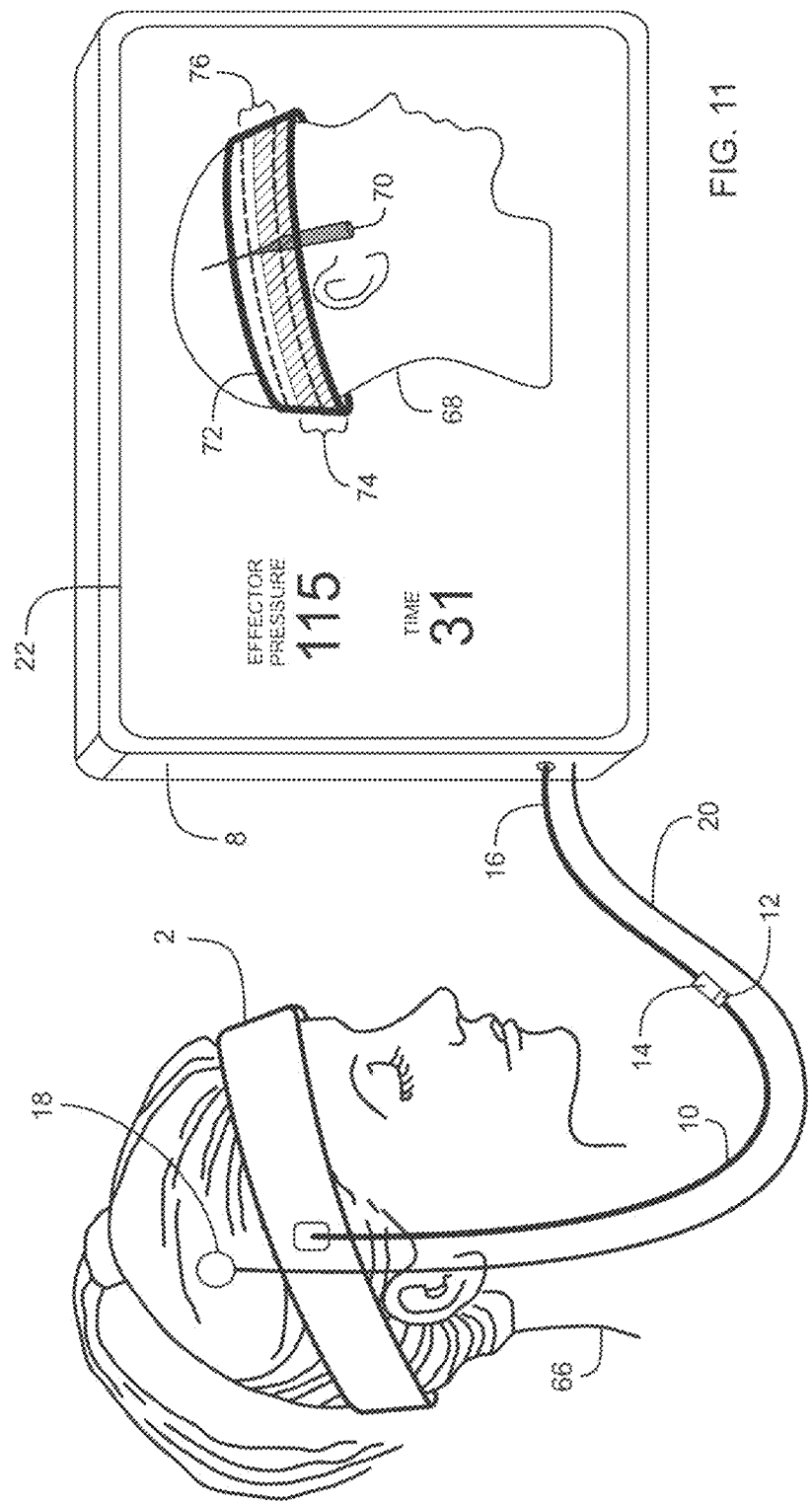
FIG. 11 is a pictorial representation of embodiments in use during a medical procedure for stopping arterial bloodflow into a region of the scalp.

FIG. 11 depicts preferred embodiments in clinical use to stop arterial blood flow into a region or portion of a patient other than an arm or a leg, specifically the scalp. In FIG. 11, dual-purpose tourniquet cuff 2 is shown applied to patient head 66 to prevent the flow of arterial blood past cuff 2 into a region of the scalp. Distal blood flow sensor 18 is shown adapted for application to the scalp distal to cuff 2, and may be used prior to the commencement of a surgical or medical procedure as described above to determine a Personalized Tourniquet Pressure. As further described above, cuff 2 may also be used as a sensor to determine a Personalized Tourniquet Pressure. For example, distal sensor 18 or cuff 2 may be used to determine a PTP prior to the administration of a chemotherapy agent in embodiments used to reduce chemotherapy related alopecia.

In FIG. 11, touch screen interface 22 is shown during the procedure time after a PTP has been established. A pictorial representation of blood penetration into the region of the scalp encircled by cuff 2 is displayed. The pictorial representation of blood penetration consists of head icon 68, artery icon 70, cuff icon 72, distance of penetration indicator 74 and safety margin indicator 76. As described further above, the pictorial representation of blood penetration past the cuff into the region of the scalp encircled by cuff 2 is continually updated during the procedure time period so that the distal edge of indicator 74 and the shape of artery icon 70 represent the current distance of penetration as determined by preferred embodiments.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An apparatus for regulating tourniquet cuff pressure based on a personalized tourniquet pressure (PTP), comprising:
    a dual-purpose tourniquet cuff having an inflatable bladder adapted to encircle a portion of a patient;
    a sensor module having a pulsation sensor communicating pneumatically with the inflatable bladder of the dual-purpose cuff for sensing and characterizing pressure pulsations indicative of a distal occlusion pressure (DOP), thereby to identify a minimum pressure at which penetration of blood past the cuff is stopped;
    a PTP estimator responsive to the pulsation sensor for producing an estimate of a PTP, wherein the estimate of the PTP is a function of the DOP;
    an effector module communicating pneumatically with the inflatable bladder of the dual-purpose cuff for maintaining pressure in the bladder near the PTP; and
    a controller selectively operating the inflatable bladder in conjunction with the sensor module and the effector module.

2. The apparatus of claim 1 wherein the portion of the patient is a limb proximal to a surgical site.

3. The apparatus of claim 1 wherein the portion of the patient is a region of the patient's scalp.

4. The apparatus of claim 1 wherein the controller operates the inflatable bladder with the sensor module during a first time period.

5. The apparatus of claim 4 wherein the controller operates the inflatable bladder with the effector module during a second time period.

6. The apparatus of claim 5 wherein the controller further operates the inflatable bladder with the sensor module for sensing and characterizing pressure pulsations during the second time period.

7. The apparatus of claim 1 further comprising a cuff identification module for alerting a user in instances when the inflatable bladder is not part of a dual-purpose cuff.

8. The apparatus of claim 1 wherein the function is a percentage of the DOP.

9. An apparatus for regulating tourniquet cuff pressure based on a personalized tourniquet pressure (PTP), comprising:
    a sensor module for estimating a distal occlusion pressure (DOP) by determining an estimated DOP equal to a minimum pressure at which penetration of blood past an applied tourniquet cuff is stopped, and measuring a first pulsation characteristic associated with the DOP;
    a controller for establishing a PTP by determining a second pressure that is greater than the DOP and that corresponds to a second pulsation characteristic that differs by a percentage from the first pulsation characteristic associated with the DOP; and
    an effector module operable during a time period for maintaining pressure in an applied tourniquet cuff near the PTP.

10. The apparatus of claim 9 wherein the percentage is a function of a magnitude of the estimated DOP.

11. The apparatus of claim 9 wherein the sensor module is also for sensing a characteristic of blood that penetrates past the applied tourniquet cuff.

12. The apparatus of claim 9 wherein the sensor module is also for sensing in an inflatable bladder of the cuff a series of pulsation characteristics from which at least one of the first and second pulsation characteristics is determined.

13. An apparatus for regulating tourniquet cuff pressure based on a personalized tourniquet pressure (PTP), comprising:
a dual-purpose tourniquet cuff having a bladder and configured to be applied to a patient at a desired location;
a controller operable during a first time period for:
estimating a minimum pressure at which penetration of blood past the applied tourniquet cuff is stopped by analyzing pressure pulsations in the bladder of the cuff that are associated with selected pressures in the bladder, thereby to identify a distal occlusion pressure (DOP) at the location and a first pulsation characteristic associated with the DOP;
establishing a PTP by determining a second pressure that is greater than the DOP and that corresponds to a second pulsation characteristic that differs by a percentage from the first pulsation characteristic associated with the DOP; and
maintaining pressure in the bladder of the dual-purpose tourniquet cuff near the PTP during a second time period.

14. The apparatus of claim 13 further comprising a noise sensor module for determining a noise level associated with pressure fluctuations in the bladder that are independent of the pressure pulsations analyzed for the estimation of DOP.

15. The apparatus of claim 14 wherein the controller causes an alert perceptible by a user to be produced if the noise level is greater than a noise threshold.

16. A method for regulating tourniquet cuff pressure based on a personalized tourniquet pressure (PTP), comprising:
estimating a distal occlusion pressure (DOP) by determining a minimum pressure at which penetration of blood past an applied tourniquet cuff is stopped;
measuring a first pulsation characteristic associated with the DOP;
establishing a PTP by determining a second pressure that is greater than the DOP and that corresponds to a second pulsation characteristic that differs by a percentage from the first pulsation characteristic associated with the DOP; and
during a procedure time period, maintaining pressure in the applied tourniquet cuff near the PTP.

17. The method of claim 16 wherein the first or second pulsation characteristic is indicative of a shape of the pulsation.

18. The method of claim 16 wherein the first or second pulsation characteristic is a maximum amplitude of pulsation.

19. The method of claim 16 wherein the percentage is a function of the magnitude of the estimated DOP.

20. The method of claim 16 wherein estimating the DOP includes sensing a characteristic of blood that penetrates past the applied tourniquet cuff.

21. The method of claim 16 wherein estimating the DOP includes sensing in an inflatable bladder of the cuff a series of pulsation characteristics from which at least one of the first and second pulsation characteristics is selected.

22. The method of claim 16 wherein the applied tourniquet cuff encircles a portion of a limb of a patient.

23. The method of claim 16 wherein the applied tourniquet cuff encircles a region of a patient's scalp.

24. A method for regulating tourniquet cuff pressure based on a personalized tourniquet pressure (PTP), comprising:
during a first time period, estimating a distal occlusion pressure (DOP) by determining a minimum pressure at which penetration of blood past an applied tourniquet cuff is stopped,
measuring a first pulsation characteristic associated with the DOP,
establishing a PTP by determining a second pressure that is greater than the DOP and that corresponds to a second pulsation characteristic that differs by a predetermined percentage from the first pulsation characteristic associated with the DOP; and
during a second time period, regulating the cuff pressure to maintain a procedure pulsation characteristic near the second pulsation characteristic.

25. The method of claim 24 wherein estimating the DOP includes sensing a characteristic of blood that penetrates past the applied tourniquet cuff.

26. The method of claim 24 wherein estimating the DOP includes sensing in an inflatable bladder of the cuff a series of pulsation characteristics from which at least one of the first and second pulsation characteristics is selected.

27. The method of claim 24 including producing an alert if the procedure pulsation characteristic is outside a predetermined range.

28. The method of claim 24 wherein the applied tourniquet cuff encircles a region of a patient's scalp.

29. A method for regulating tourniquet cuff pressure based on a personalized tourniquet pressure (PTP), comprising the steps of:
applying a tourniquet cuff having a bladder to a patient at a location;
during a first time period:
estimating a minimum pressure at which penetration of blood past the applied tourniquet cuff is stopped by analyzing pressure pulsations in the bladder of the cuff that are associated with selected pressures in the bladder, thereby to identify a distal occlusion pressure (DOP) at the location;
establishing a PTP by determining a second pressure that is greater than the DOP and that corresponds to a second pulsation characteristic that differs by a percentage from a first pulsation characteristic associated with the DOP; and
during a second time period maintaining pressure in the bladder of the applied tourniquet cuff near the PTP.

30. The method of claim 29 wherein applying a tourniquet cuff comprises applying the tourniquet cuff at a location proximal to a portion of a limb.

31. The method of claim 29 wherein applying a tourniquet cuff comprises applying the tourniquet cuff at a location proximal to a region of a patient's scalp.

32. The method of claim 29 further comprising determining a noise level associated with pressure fluctuations in the bladder that are independent of the pressure pulsations analyzed for the estimation of DOP.

33. The method of claim 29 wherein establishing comprises compensating for effects of a noise level above a threshold level.

34. The method of claim 29 wherein determining a noise level comprises producing an alert perceptible by a user if the noise level is greater than a noise threshold.

35. The method of claim 29 wherein the pressure fluctuations are associated with muscle contractions during the first time period.

* * * * *